United States Patent [19]

Penn

[11] 4,048,316
[45] Sept. 13, 1977

[54] COMPOSITION FOR ANTAGONIZING THE NARCOTIC EFFECTS OF BARBITURATE ADDICTION AND WITHDRAWAL EFFECTS, AND FOR TREATMENT OF BARBITURATE POISONING

[76] Inventor: Nathar W. Penn, 463 Glendale Road, Wyckoff, N.J. 07481

[21] Appl. No.: 447,659

[22] Filed: Mar. 4, 1974

[51] Int. Cl.² .......................................... A61K 31/505
[52] U.S. Cl. .................................. 424/251; 424/255; 424/263; 424/266
[58] Field of Search ........................................ 424/251

[56] References Cited

U.S. PATENT DOCUMENTS 3,773,955  11/1973  Pacter et al. ........................... 424/10

FOREIGN PATENT DOCUMENTS 808,269  1/1959  United Kingdom ................... 424/10

OTHER PUBLICATIONS

Nakagawa, Chemical Abstracts 54:21390a (1960).
Wenzel et al., Chemical Abstracts 49:4177d (1955).
Batt, Chemical Abstracts 55:10580e (1961).
Batt, Chemical Abstracts 55:17760 (1961).
Miller, Chemical Abstracts 49:8302i (1955).
Merck Index, 8th Edition, (1968), pp. 729, 892, 1036 and 1050.

*Primary Examiner*—Norman A. Drezin
*Attorney, Agent, or Firm*—W. Lee Helms

[57] ABSTRACT

The invention is based on the discovery, after long study and many test operations, that the combination of five chemical elements, towit 5-hydroxymethylcytosine, thymine, nicotamide, pyridoxal, and thiamine, is effective in antagonizing the narcotic effects of barbiturates, and that each one is essential, in the combination, for positive result. Although thymine per se long has been known as increasing the action of barbiturates, tests of the said composition established that thymine has an unexpected and essential function therein, its omission rendering the composition ineffective. These tests were directly made by the present applicant, with corroboration as to every detail thereof by the Chief of the Section of Neurochemistry, New York State Institute of Neurochemistry and Drug Addiction, established by the State of New York, and operating under its control.

2 Claims, No Drawings

COMPOSITION FOR ANTAGONIZING THE NARCOTIC EFFECTS OF BARBITURATE ADDICTION AND WITHDRAWAL EFFECTS, AND FOR TREATMENT OF BARBITURATE POISONING

Barbiturates are in three classes, towit: ultra-short acting, long acting, and intermediate. Although it is generally accepted that substances which antagonize one barbiturate will antagonize another, tests, as referred to above, show full effectiveness of the present composition with each of the barbitol classes. towit: the ultra-short acting, exemplified by hexobarbital; the long-acting, exemplified by phenobarbital; and the intermediate acting, exemplified by pentobarbital.

The tests were made in accordance with practice now accepted as determining the effectiveness of materials for antagonizing drugs in man, and for chemicals, and also for antagonizing carcinomas, by tests on mice or rates, examples being cited in the footnote below **.

** 1. Drs. Cohn, Taylor & Yamakaya, Pittsburgh University School of Medicine July 30, 1973, Research Communications in Chemical Pathology and Pharmacology, Vol. 6, No. 2, pp 435–443 "A major aim of this research is to determine the basis for the use of dibutryl cylcic in man"
2. Drs. Silbergeld and Goldberg, to investigate the result of lead acetate in children, by treatment of a mitigating material on mice — The Johns Hopkins University School of Hygiene and Public Health; Life Sciences, Vol. 13. pp. 1275–1283 September 1973. U.S. Pat. No. 3,577,558, etc.

THE ULTRA-SHORT ACTING BARBITAL, EXEMPLIFIED BY HEXOBARBITAL, TREATED WITH THE COMPOSITION

EXAMPLE 1

Twenty male Swiss Albino Mice, of weight 20–25 gms. were intraperitoneally injected each with 150 mg/kg of hexobarbitol in 0.2 ml of water per 20 gm mouse, adjusted proportionally for weight. The onset of narcosis was judged by the ability of the animal to right itself when placed on its back. As each animal lost this reflex, it was placed on a paper sheet with the time written below it. Between 15 and 20 minutes thereafter 10 of the animals were each injected with the antagonizing composition of the present application, being:

| | |
|---|---|
| 2.76 mg of 5-hydroxymethyl cytosine; | |
| 1.16 mg thymine | |
| 1.02 mg of pyridoxal hydrochloride; | |
| 0.24 mg nicotinamide; | In 0.8 ml water |
| 0.16 mg thiamine hydrochloride. | per 20 gm weight. |

Recovery time was noted when the animal turned itself over. Each animal was checked over after such recovery by endeavoring to place it on its back. It was not considered to have fully recovered if it did not right itself within 2 minutes. The sleeping time for the controls, not receiving the barbitol mitigating composition, was 184 minutes, whereas the 10 animals receiving the composition had an average sleeping time of 101 minutes, the standard gauge of the different sleeping times being $p < 0.02$.

THE INTERMEDIATE-ACTING BARBITAL EXEMPLIFIED BY PENTOBARBITAL, TREATED WITH THE COMPOSITION

EXAMPLE 2

Thirty mice weighing 20–25 gm were injected intraperitoneally with 1.0 mg. pentobarbital in 0.2 ml of water per 20 gm mouse, adjusted proportionally for weight. Fifteen of the mice were as to each mouse, and between 15 and 20 minutes after the barbital injection, injected with the composition of Example 1 above and hence with the same proportions of its elements. The assay of the 30 mice, all males, gave an average sleeping time of 239 minutes for the 15 animals treated with the composition, 420 minutes for the untreated 15 animals. Statistical analysis of the difference between the two groups gave a value of $p < 01$.

THE LONG ACTING BARBITAL, EXEMPLIFIED BY PHENOBARBITAL, TREATED WITH THE COMPOSITION

EXAMPLE 3

Twenty male rats of laboratory stock, weighing 200–300 gms were used in standard sleeping time assay. Phenobarbital was injected intraperitoneally to each of the rats at the level of 80 mg/kg. This larger amount of drug requires a larger amount of the antidote, correspondingly. Each animal was injected twice to get a maximal level of antidote administered. Ten of the animals were used as controls, and after said time of administration of the pentobarbital, and when the animals had lost their body- righting reflexes, the 10 remaining animals were intraperitoneally injected with the antagonizing composition. The composition of administration was the same as in the previous examples, but 12 ml was given in two 6 ml portions per 200 gm rat, as saline mixture. Thus for each of the treated rats the injection of 16 mg phenobarbital was followed by administration of 55.2 mg of 5-hydroxymethylcytosine; 23.3 thymine; 20.4 mg pyridoxal hydrochloride; 4.8 nicotinamide; and 3.3 mg of thiamine hydrochloride, in a total of 12.0 ml. 6 ml of the composition was given intraperitoneally when the animal lost its body righting reflex, the remaining 6 ml was injected one-half hour later. The results were as follows:

| | |
|---|---|
| Sleeping time of the rats not receiving the antagonizing composition | 598 minutes. |
| Sleeping time of the rats receiving the composition | 361 minutes. |

Analysis by standard test formula, $p < 0.01$.

COMPARATIVE TESTS OF THE COMPOSITION, AND OF THE COMPOSITION WITHOUT THE THYMINE, SHOW THAT THYMINE IS A REQUIRED ELEMENT IN THE COMPOSITION

EXAMPLES 4 and 5

To a fluid carrier, towit physiological saline of 15 cc was added the following:
  69.0 mg hydroxymethyl cytosine,
  4.0 mg thiamine hydrochloride..
  25.5 mg pyridoxal hydrochloride,
  6.0 mg nicotinamide.

The mixture was divided into equal parts, and to the second one half proportion was added 14.3 thymine, the first half of the mixture being used as a control.

The control half of the mixture had the following values per 20 gm mouse:
  2.76 mg Hydroxymethyl cytosine,
  0.16 mg thiamine hydrochloride,
  1.02 mg pyridoxal hydrochloride,
  0.24 mg nicotinamide.
in 0.6 saline.

The second and treatment half part added a value per 20 gm mouse of 1.14 mg thymine.

Sodium pentobarbital, 1.2 mg per 20 gm mouse was dissolved in physiological saline to give 6.0 mg per ml and injected intraperitonically into both the control and the remaining 10 mice. As each mouse lost its righting reflex, the 10 mice were intraperitoneally injected with the first stated composition, lacking thymine, and constituting controls. The remaining 10 mice were intraperitoneally injected with the same composition with the added thymine.

The difference in sleeping time between the 10 control mice, lacking thymine, and the 10 treated mice with added thymine was highly significant. The sleeping time of the control mice was 401 minutes, and the sleeping time of the mice receiving the same components plus thymine was 211 minutes. Statistical analysis gave $p < 0.01$ by the Standard Student test.

These Examples were directly performed by the applicant with corroboration by Dr. Neville Marks, who closely checked all steps and parameters of the work.

As to each of the stated Examples, nicotinic acid can be substituted for nicotinamide, giving the same results; and pyridoxal phosphate and pyridoxamine can be substituted for pyridoxal hydrochloride.

It is postulated that the composition is not only applicable to barbiturates, but to similar other drugs resulting in degrees of narcosis. Particularly after administration of the composition has effected marked reduction of such barbiturate action, whereupon the treatment may be continued with the composition of 5 HMC and thymine alone, and until the physiological condition is normal. However, the full composition should be employed at the start of treatment of definite addiction, and continued until there has been affirmative indication that the addiction force has been weakened to a substantial degree. In the case of narcotic poisoning it is preferred, as to treatment with the composition, that the full composition at maximum proportions of the composition constituents be employed until the patient's severe reactions to the poisoning definitely have been substantially brought down.

As to the dosage of the composition with respect to adults and adolescents, the fact that each one of the constituents of the composition is non-toxic below a high point beyond which physicians would not prescribe, and which is well known, a wide range between the minimal and the maximum effective dosage is permitted, of which the following statement will be a guide:

| Adult and Adolescents Minimal and Maximum dosage : | | |
|---|---|---|
| 1. For Intravenous Treatment: | | |
| Composition constituent | Minimal: | Maximum: |
| 5-HMC | 0.7 gm | 1.4 gm, and controlled by level indicated in therapy. |
| Thymine | 0.27 gm | 0.55 gm, and controlled as above. |
| Pyridoxal hydrochloride | 0.2 gm | 0.5 gm |
| Nicotinamide | 0.5 gm | 3.5 gm |
| Thiamine hydrochloride | 0.01 gm | 0.09 gm |
| 2. For oral use, as in tablet or capsule form: | | |
| Composition constituent: | | |
| 5-HMC | 1.4 gm | 2.8 gm |
| Thymine | 6.55 gm | 1.2 gm |
| Pyridoxal hydrochloride | 0.2 gm | 0.5 gm |
| | Oral Use continued: | |
| | Minimal: | Maximum: |
| Nicotinamide | 0.5 gm | 2.0 gm |
| Thiaminehydrochloride | 0.04 gm | 0.09 gm |

In addition to the stated administration of the composition by injection intraperitoneally, and by oral administration, as by tablet, powder or capsule, the composition may be administered in solution by stomach tube, etc.

The action of the composition can readily be understood in the bio-chemical and pharmaceutical fields, by the fact that it supplies the components required to remove the narcotic drug from its combination with deoxyriboneucleic acid, thereby rectifying cellular metabolism, and the reactions of the patient receiving the drug invariably indicates to the physician the extent of drug intake, and volume of the antagonizing composition which should be employed. As stated above, in the case of narcotic poisoning where the patient's reactions are very severe, or in the case of addiction where the intake of the narcotic drug is of substantial amount daily, the full amount of the composition scheduled above as "maximum" should be used, but controlled by the physician's decided therapy for each case.

When the treatment of a patient by the composition has resulted in substantial reduction of the narcotic drug, it has been found that only two of the composition constituents, towit 5-HMC and thymine need be continued in the treatment, and preferably once per 24 hours with the two components in amount about the middle of the maximum amount in the above schedule for both intravenous and "oral" administration, until the patient requires no continued daily treatment.

Having described my invention, what I claim and desire to protect by Letters Patent, is as follows:

1. An intravenous composition for antagonizing the narcosis effect of barbiturates which comprises.
   5-hydroxymethylcytosine 0.7 to 1.4 Gm
   thymine 0.27 to 0.55 Gm
   pyridoxal hydrochloride 0.2 to 0.5 Gm
   nicotinamide 0.5 to 2.0 Gm
   thiamine hydrochloride 0.04 to 0.09 Gm 2. An oral composition for antagonizing the narcosis effect of barbiturates which comprises
   5-hydroxymethylcytosine 1.4 to 2.8 Gms
   thymine 0.55 to 1.2 Gms
   pyridoxal hydrochloride 0.2 to 0.5 Gms
   nicotinamide 0.5 to 2.0 Gms
   Thiamine hydrochloride 0.04 to 0.09 Gms.

* * * * *